United States Patent
Noll et al.

(10) Patent No.: US 8,527,102 B2
(45) Date of Patent: Sep. 3, 2013

(54) CONTROLLING THE COOLING OF FERMENTERS OF A BIOFUEL PRODUCTION PLANT

(75) Inventors: Patrick D. Noll, Richardson, TX (US); James F. Bartee, Stilesville, IN (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 265 days.

(21) Appl. No.: 12/827,923

(22) Filed: Jun. 30, 2010

(65) Prior Publication Data

US 2012/0004755 A1   Jan. 5, 2012

(51) Int. Cl.
*G06F 19/00* (2011.01)

(52) U.S. Cl.
USPC ......... 700/282; 700/104; 700/291; 435/286.5

(58) Field of Classification Search
USPC .................. 700/184, 282, 291; 435/286.5
See application file for complete search history.

(56) References Cited

U.S. PATENT DOCUMENTS

| | | |
|---|---|---|
| 2008/0104003 A1 | 5/2008 | Macharia et al. |
| 2008/0108048 A1 | 5/2008 | Bartee et al. |
| 2008/0109100 A1 | 5/2008 | Macharia et al. |
| 2008/0109200 A1 | 5/2008 | Bartee et al. |
| 2008/0167852 A1 | 7/2008 | Bartee et al. |

*Primary Examiner* — Michael D Masinick
(74) *Attorney, Agent, or Firm* — Fletcher Yoder, P.C.; William R. Walbrun; John M. Miller (57) ABSTRACT

According to various embodiments, a biofuel production system includes a plurality of parallel-operated fermenters, a cooling tower water system configured to supply cooling water to the plurality of parallel-operated fermenters, a chiller water system configured to supply chiller water to the plurality of parallel-operated fermenters, and a cooling system coupled to the plurality of parallel-operated fermenters, the cooling tower water system, and the chiller water system. The cooling system controls the flow rates of the cooling water and the chiller water to the plurality of parallel-operated fermenters based upon temperatures of fermentation products of the fermenters.

25 Claims, 6 Drawing Sheets

CONTROLLING THE COOLING OF FERMENTERS OF A BIOFUEL PRODUCTION PLANT

BACKGROUND

The invention relates generally to control systems, and more particularly to process control employing novel techniques for controlling the cooling of batch processes of a biofuel production plant.

A biofuel production plant may include one or more batch processes. An example of a batch process is the fermentation of a starch source to produce ethanol and other by-products in the presence of yeast and other enzymes in fermenters. Fermentation may be exothermic and the heat generated by fermentation may negatively affect the yeast. Thus, the contents of the fermenters are cooled to maintain the temperature of the fermenter within a range acceptable for the yeast. The biofuel production plant may use a variety of methods for cooling the fermenters, which may include circulating the fermenter contents through a heat exchanger cooled by water. Several sources of cooling water may be used and the sources may differ in terms of temperature and available flow rate. In addition, each of the fermenters of the biofuel production plant may be operating at different points of a batch cycle. Thus, the plant-wide consumption of cooling water varies and there may not be sufficient cooling water to provide maximum cooling to all fermenters simultaneously. Existing methods of controlling cooling in biofuel production plants suffer from disadvantages that may result in decreased ethanol production and inefficient use of yeast.

BRIEF DESCRIPTION

The present invention provides novel techniques for controlling the cooling of batch processes of a biofuel production plant. In particular, the present techniques are presented in the context of a series of parallel fermenters of the biofuel production plant. More particularly, in various embodiments, the cooling may be accomplished using cooling tower water, chilled water, or both. However, it should be borne in mind that the invention may be applied in a wide range of contexts, in a variety of plants, and in any desired industrial, commercial, private, or other setting.

In accordance with one aspect of the present disclosure, a biofuel production system includes a plurality of parallel-operated fermenters, a cooling tower water system configured to supply cooling water to the plurality of parallel-operated fermenters, a chiller water system configured to supply chiller water to the plurality of parallel-operated fermenters, and a cooling system coupled to the plurality of parallel-operated fermenters, the cooling tower water system, and the chiller water system. The cooling system controls the flow rates of the cooling water and the chiller water to the plurality of parallel-operated fermenters based upon temperatures of fermentation products of the fermenters.

In accordance with another aspect, a biofuel production system, for use in a facility having a plurality of parallel-operated fermenters, a cooling tower water system, and a chiller water system, includes a cooling system coupled to the plurality of parallel-operated fermenters, the cooling tower water system, and the chiller water system. The cooling system controls the flow rates of the cooling water and the chiller water to the plurality of parallel-operated fermenters. The biofuel production system also includes a process controller configured to determine desired flow rates of the cooling water and the chiller water to each of the parallel-operated fermenters.

In accordance with a further aspect, a biofuel production system includes a plurality of parallel-operated fermenters, a cooling tower water system configured to supply cooling water to the plurality of parallel-operated fermenters, a chiller water system configured to supply chiller water to the plurality of parallel-operated fermenters, and a cooling system coupled to the plurality of parallel-operated fermenters, the cooling tower water system, and the chiller water system. The cooling system controls supply of water to the parallel-operated fermenters during normal operation, and provides prioritized supply of water from the chiller water system to any fermenter with a temperature approaching or meeting a threshold temperature.

In accordance with still another aspect, a biofuel production system, for use in a facility having a plurality of parallel-operated fermenters, a cooling tower water system, and a chiller water system, includes a cooling system coupled to the plurality of parallel-operated fermenters, the cooling tower water system, and the chiller water system. The cooling system controls the flow rates of the cooling water and the chiller water to the plurality of parallel-operated fermenters. The biofuel production system also includes a process controller that controls supply of water to the parallel-operated fermenters during normal operation, and provides prioritized supply of water from the chiller water system to any fermenter with a temperature approaching or meeting a threshold temperature.

In accordance with yet another aspect, a method for controlling the cooling of a plurality of parallel-operated batch processes in a production plant using a cooling system comprising a plurality of cooling fluids includes determining operating variables of the plurality of parallel-operated batch processes and the cooling system, determining constraints of the plurality of parallel-operated batch processes and the cooling system, determining desired flow rates of the plurality of cooling fluids through the plurality of parallel-operated batch processes based upon the determined operating variables, constraints, and an overall optimization objective, and controlling the flow rates of the plurality of cooling fluids through the plurality of parallel-operated batch processes based upon the desired flow rate determinations.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
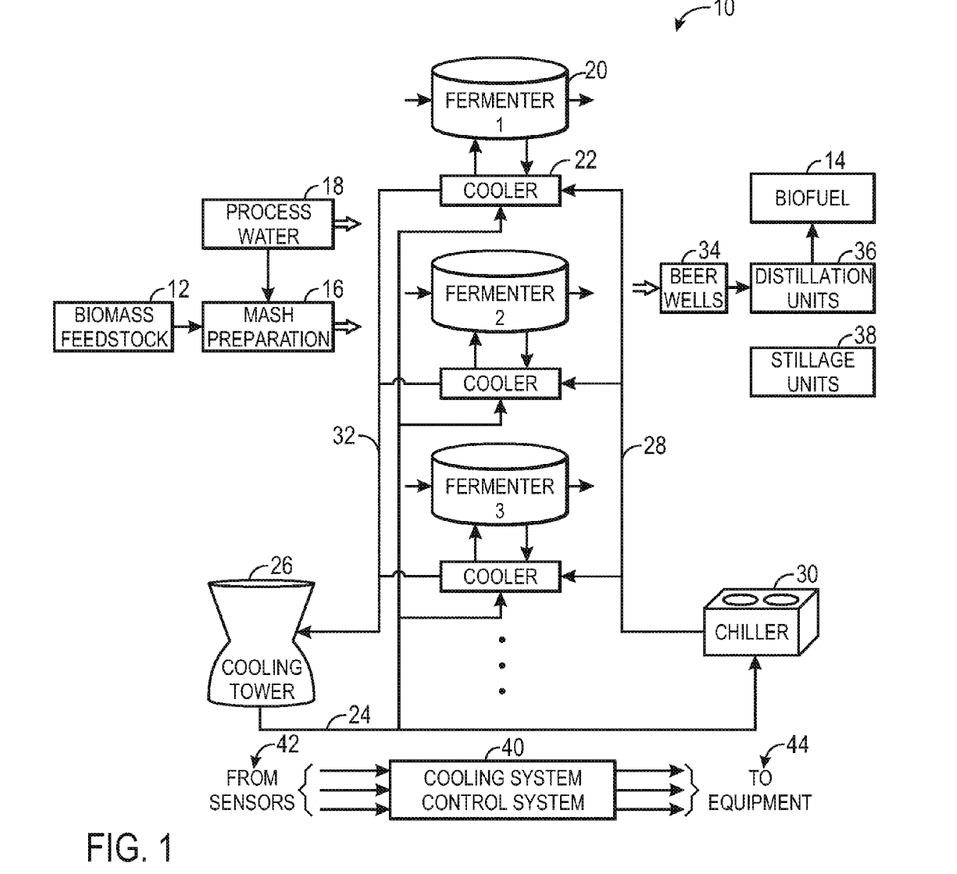
FIG. 1 is a diagram of an exemplary biofuel production plant.

FIG. 1 is a diagram of an exemplary biofuel production plant 10, illustrating how biomass feedstock 12 may be processed through several stages to produce biofuel 14. One or more of the various stages in the biofuel production plant 10 may be susceptible to exemplary methods of controlling batch processes as described in detail below. In addition, certain embodiments may be applicable to continuous processes. Biomass 12 may first be provided to a mash preparation process 16, where process water 18 (which may include recycled water) may be added and the biomass 12 may be broken down to increase the surface area-to-volume ratio. Examples of biomass 12 include, but are not limited to, corn, sorghum, milo, wheat, or combinations thereof. This increase in surface area may allow for sufficient interaction of the water and biomass 12 surface area to achieve a solution of fermentable sugars in water. The mixture, a biomass 12 and water slurry, may be cooked to promote an increase in the amount of contact between the biomass 12 and water in solution and to increase the separation of carbohydrate biomass from non-carbohydrate biomass. The output of the mash preparation process 16 (i.e., the fermentation feed or mash) may then be sent to a fermentation process, where one or more fermenters 20 may operate to ferment the biomass/water mash produced by the mash preparation process 16.

In the fermenters 20, yeast and enzymes may convert the biomass 12 into a biofuel 14 and by-products, such as carbon dioxide, water, and non-fermentable biomass (solids). Biofuel production plants 10 may typically have anywhere between 3 to 7 fermenters 20, although fewer or greater numbers of fermenters 20 may be used depending on the capacity of the plant 10. Heat generated by the exothermic fermentation reaction is removed by coolers 22, which may include heat exchangers that transfer heat from the process to a cooling medium, or cooling fluid, because of a temperature gradient. One cooling medium that may be used is cooling tower water 24 supplied from one or more cooling towers 26. Cooling towers transfer process heat from the water to the atmosphere using either evaporative cooling or heat transfer. Alternatively, chiller water 28 from a chiller 30 may be used as the cooling medium. Chillers 30 remove process heat from water using a refrigeration cycle in which a refrigerant, such as ammonia, sulfur dioxide, carbon dioxide, or non-halogenated hydrocarbons, undergoes a phase change from gas to liquid and back. Chiller water 28 may be cooler than cooling tower water 24. Thus, chiller water 28 may be used to supplement cooling tower water 24 when additional cooling is needed. However, chiller water 28 may be more expensive or available at lower flow rates than cooling tower water 24. In addition, the chiller 30 may have a minimum operating flow rate below which the chiller is shut down. As shown in FIG. 1, after cooling tower water 24, chiller water 28, or both passes through the coolers 22, warm water, or return water, 32 returns to the cooling tower 26. After being cooled, the cooling tower water 24 may be sent back to the coolers 22 for additional heat transfer. If the chiller 30 is being used, then some of the cooling tower water 24 may be used to produce chiller water 28. The piping and equipment associated with the paths of water through the coolers 22, cooling tower 26, and chiller 30 may be referred to as a cooling system.

As shown in FIG. 1, the fermentation process is a batch process and may include multiple fermenters 20 and coolers 22 operating in parallel (indicated by the vertical ellipsis). The batch start times may be staggered in order to optimize the utilization of the capacity of the beer wells 34 and smoothly distribute the flow of fermentation feed to the fermentation process and the flow of biofuel 14 and stillage as output from the fermentation process.

After being temporarily stored in the beer wells 34, the output from the fermenters 20 may be sent to a distillation process, e.g., one or more distillation units 36, to separate biofuel 14 from water, carbon dioxide, and non-fermentable solids. If the biofuel 14 has to be dehydrated to moisture levels less than 5% by volume, the biofuel 14 may be processed through a processing unit that may include a molecular sieve or other suitable separation equipment. The finalized biofuel 14 may then be processed to be denatured and unfit for human consumption.

The distillation units 36 separate the biofuel 14 from water and other components that may be transported with the biofuel into the distillation units. Water may be used in the form of steam for heat and separation, and the condensed water may be recycled back to the mash preparation process 16. Stillage (non-fermentable solids and yeast residue), the heaviest output of the distillation units 36, are sent to stillage processing units 38 for further development of co-products from the biofuel 14 production process.

The stillage processing units 38 may separate additional water from the cake solids and recycle the water back to the mash preparation process 16. The water may include both dissolved and suspended solids. Several stillage processing options may be utilized, including: (1) selling the stillage with minimal processing and (2) further processing the stillage by separating moisture from the solid products via one or more centrifuge units. Using the centrifuge units, the non-fermentable solids may be transported to dryers for further moisture removal. A portion of the stillage liquid (concentrate) may also be recycled back to the fermenters 20. However, the bulk of the flow may generally be sent to evaporator units, where more liquid may be separated from the liquid stream, causing the liquid stream to concentrate into syrup, while solid stillage may be sent to a drying process, e.g., using a drying unit or evaporator, to dry the solid stillage to a specified water content. The syrup may then be sent to a syrup tank. Syrup in inventory may be processed using a number of options. For instance, the syrup may be: (1) sprayed in dryers to achieve a specified color or moisture content, (2) added to the partially dried stillage product, or (3) sold as a separate liquid product. The evaporator units may have a water by-product stream that is recycled back to the mash preparation process 16.

A variety of sensors, or process instruments, may be placed throughout the cooling system of the biofuel production plant 10. Such sensors may measure process data or operating variables, such as temperatures, flow rates, pressures, and/or levels, of the cooling system or of other processes in the plant 10. Alternatively, the operating variables may be determined using inferential models, laboratory values, or combinations thereof. Sensor output 42 may be transmitted to a cooling system control system 40. Plant operators may be able to monitor the sensor output 42 and interact with the control system 40 to provide new set points, for example. Based on sensor output 42, input from operators, programming, and/or other inputs, the control system 40 transmits output signals 44 to the process. The output signals 44 may be used to manipulate equipment, such as valves, motors, and/or pumps. In addition, the output signals 44 may be used to turn the chiller 30 on or off.

Figure 2:
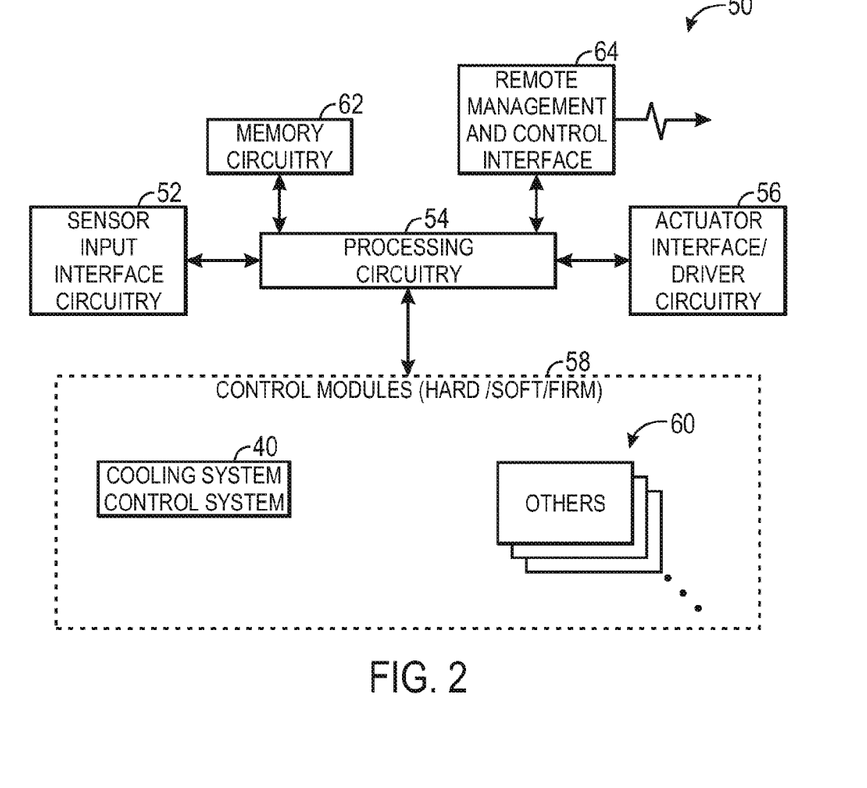
FIG. 2 is a diagram of a control system capable of implementing an exemplary method of controlling fermenter cooling.

FIG. 2 shows a diagram of a control system 50 for the biofuel production plant 10 capable of implementing an exemplary method of controlling the cooling of fermenters 20. For example, sensor input interface circuitry 52 may organize input from a variety of sensors and configure it into a recognizable form, such as a 4-20 mA signal, for processing circuitry 54. In addition, the processing circuitry 54 may send queries or adjust settings of the sensors through the interface circuitry 52. Similarly, actuator interface and/or driver circuitry 56 may organize output from the processing circuitry 54 to ensure transmission to the correct device and/or transform the output into a compatible format. The actuators and/or drivers may also provide status information back to the processing circuitry 54. Connected to the processing circuitry 54 may be one or more control modules 58, which may exist as hardware, software, or firmware. The control modules 58 serve to separate the tasks performed by the processing circuitry into smaller programs that may be easier to install, modify, debug, upgrade, and/or replace without disrupting the overall operation of the biofuel production plant 10. For example, the cooling system control system 40 may be one of the control modules 58. In addition, there may be one or more other control modules 60 depending on the complexity or architecture of the biofuel production plant 10.

The processing circuitry 54 of FIG. 2 may also communicate with memory circuitry 62 that can store processed data or data to be processed by the processing circuitry 54. It should be understood that any type of computer accessible memory device capable of storing the desired amount of data and/or code may be utilized in the control system 50. For example, the memory circuitry 62 may include one or more memory devices, such as magnetic, solid state, or optical devices, of similar or different types, which may be local and/or remote to the control system 50. The memory circuitry 62 may store data, processing parameters, and/or computer programs having one or more routines for performing the processes described herein. Finally, information may be shared between a remote management and control interface 64 and the processing circuitry 54. The interface 64 enables operators, engineers, and/or management at a remote location to monitor and/or interact with the processing circuitry 54.

Figure 3:
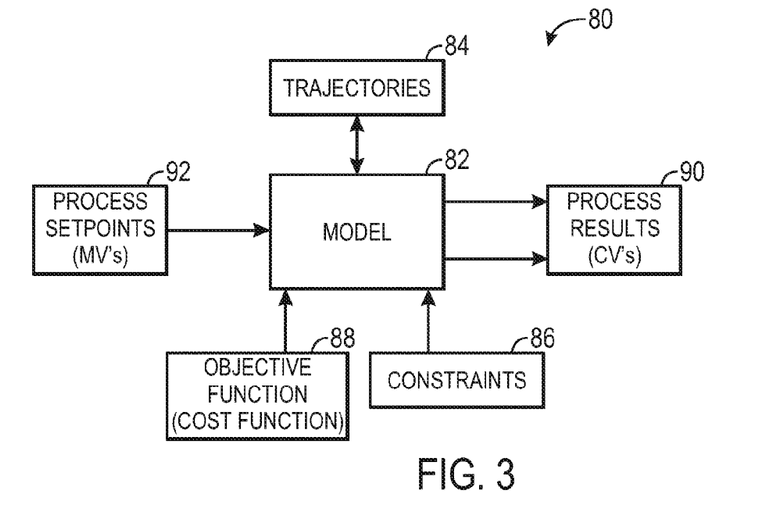
FIG. 3 is a diagrammatical representation of a dynamic multivariable predictive model controller capable of implementing an exemplary method of controlling fermenter cooling.

FIG. 3 illustrates a dynamic multivariable predictive model controller 80, which may govern the control actions implemented by the processing circuitry 54 of FIG. 2. For example, one of the control actions may be the control of the cooling of the fermenters 20. The dynamic predictive model may define mathematical relationships that include not only steady state relationships, but also time varying relationships required for each parameter change to be realized in an output. In other words, a model 82 may not only define how changes in certain process variables affect other process variables, but also rates at which such changes occur. Based on such relationships, the model 82 may derive or predict one or more anticipated trajectories 84 representing desired future values or set points for particular process variables over a time period. The trajectories 84 may be determined based at least partially on certain operating constraints 86 imposed on the controller 80 as well as one or more objective functions 88 associated with the controller 80.

Turning to the constraints 86 and objective functions 88 in more detail, the constraints 86 may include controllable constraints (e.g., those that a process has the ability and discretion to change) as well as external constraints (e.g., those outside of the process itself). Examples of constraints include, but are not limited to, process constraints, energy constraints, equipment constraints, legal constraints, operator-imposed constraints, or combinations thereof. Essentially, the constraints 86 imposed on a particular controller 80 may be representative of limits by which a controller 80 may manipulate certain manipulated variables (MV's) in controlling a process. The objective function 88 may be a mathematical relationship that defines or sets the goal or goals for the overall optimization of the process (or sub-processes within a process). In general, the objective function 88 may provide one or more consistent numerical metrics by which a process or sub-process strives to achieve and over which the performance of the process or sub-process may be measured or evaluated. The objective function 88 may be defined in terms of either objectives to be obtained or maximized or costs to be minimized, or both. Thus, the model 82 may attempt to achieve one or more process results 90 or targets (i.e., controlled variables, or CV's) based on the control or manipulation of process set points 92 for one or more other process variables (MV's) in accordance with the aforesaid trajectories 84, constraints 86, and/or objective function 88 associated with the controller 80.

For example, an exemplary cooling system control system 40 may perform several different steps to control the cooling of the fermenters 20 using cooling tower water 24 and chiller water 28. First, the control system 40 may be configured to consider the temperature of the fermenter 20 as one of the operating variables. Second, the control system 40 may be configured such that the temperature of the cooling tower water 24 is one of the constraints 86. In addition, one of the objective functions 88 may be to minimize an economic cost of energy utilized in the cooling system. An additional objective function 88 may be to maximize an economic value of products of the biofuel production plant 10, such as biofuel 14, or to achieve a target or maximum throughput of biofuel 14. Combining the two objective functions 88, an overall optimization objective may be to reduce energy costs per unit mass of biofuel 14 produced by the production plant 10. Third, based on the operating variables, constraints 86, and objective functions 88, the control system 40 may determine optimal flow rates of cooling tower water 24 and chiller water 28. Finally, the control system 40 may control the flow rates based on the optimal flow rate determinations. In certain embodiments, the control system 40 may cyclically repeat the above steps and in further embodiments, the steps may be performed sequentially or simultaneously.

Figure 4:
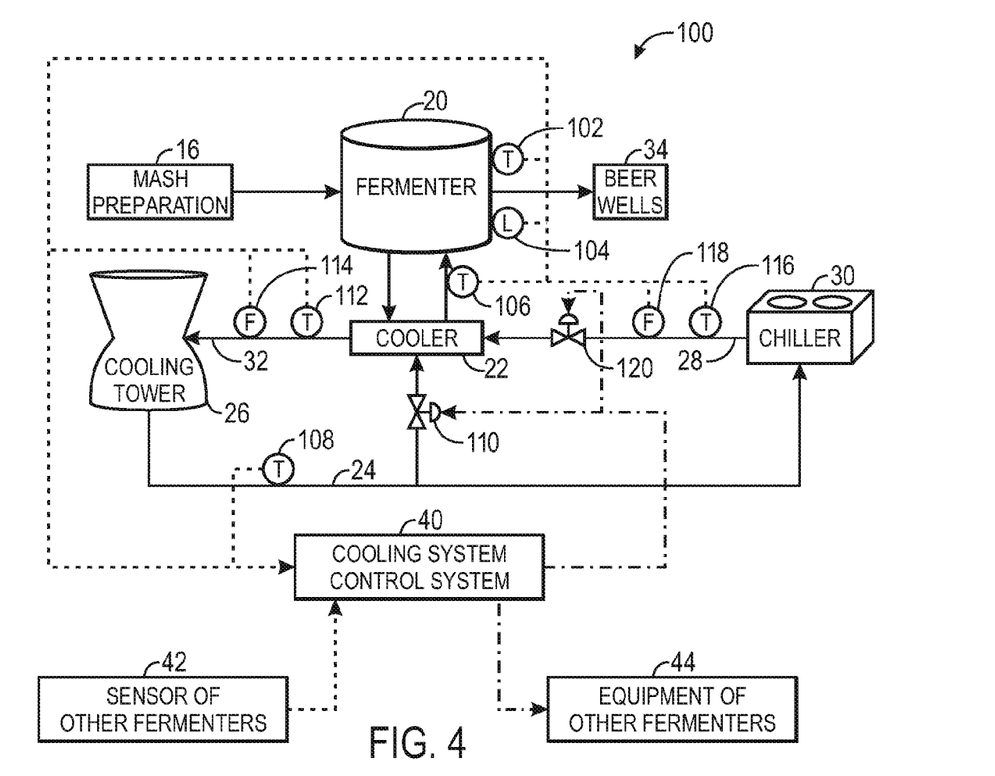
FIG. 4 is a diagram of components of a single fermenter of the biofuel production plant of FIG. 1 configured to implement an exemplary method of controlling fermenter cooling.

FIG. 4 is a more detailed process flow diagram of components of a single fermenter 20 of the biofuel production plant 10 of FIG. 1, illustrating various sensors and valves of the cooling system control system 40. Turning first to the fermenter 20, it may have a bulk temperature sensor 102 and a level sensor 104. As the volume of the fermenter 20 may be large, e.g. between approximately 1.9 megaliters to 4 megaliters, the temperature sensor 102 may indicate the bulk temperature of the fermenter contents and not localized temperature changes away from the temperature sensor 102. The level sensor 104 may be used to indicate that the correct amounts of materials have been charged and to indicate that the fermenter 20 is empty after the contents have been transferred to the beer wells 34, a process known as a drop. Next, a recirculation temperature sensor 106 may be provided on the line passing from the cooler 22 to the fermenter 20. A pump (not shown) may be used to circulate material from the fermenter 20, to the cooler 22, and back to the fermenter 20. The temperature downstream of the cooler 22 indicated by recirculation sensor 106 should be less than that indicated by bulk temperature sensor 102 because of the heat removed by the water passing through the cooler 22. In addition, the recirculation sensor 106 may be more responsive to temperature changes than the bulk sensor 102.

Moving to the cooling tower 26 of FIG. 4, a cooling tower water supply temperature sensor 108 may be provided on the outlet line from the tower 26. This sensor 108 indicates the temperature of the cooling tower water, or supply water, 24 supplied to the cooler 22 and the chiller 30, if operating. A cooling tower water control valve 110 may be provided on the line from the cooling tower 26 to the cooler 22 to automatically control the flow rate of cooling tower water 24. On the outlet line for the warm water 32 from the cooler 22 may be a return water temperature sensor 112 and a return water flow rate sensor 114. The temperature of the return water 32 should be higher than that of the supply water 24 because of the heat transferred to the return water 32 from the fermentation reaction. Moving to the chiller 30, a chiller water supply temperature sensor 116 and a chiller water flow rate sensor 118 may be on the outlet line for the chiller water 28. The temperature of the chiller water 28 should be lower than that of the cooling tower water 24 because of the refrigeration performed by the chiller 30. A chiller water control valve 120 may be provided on the line from the chiller 30 to the cooler 22 to automatically control the flow rate of chiller water 28.

As shown in FIG. 4, the output from all of the sensors (indicated by the dashed lines) is transmitted to the cooling system control system 40. Although shown as interconnecting, the signals from the sensors may pass through separate electrical conductors to an interface and then to the control system 40. In addition, output signals from the control system 40 are transmitted to both of the control valves 110 and 120 (indicated by the dashed and dotted lines) to achieve optimal flow rates. Again, although the lines are shown interconnecting, the signals may pass from the control system 40, through an interface, and then through separate electrical conductors to each control valve. Alternatively, wireless technology may be used to replace any or all of the electrical conductors. In addition, data from the sensors 42 of other fermenters may also be transmitted to the control system 40 and output signals transmitted to the control valves or other equipment 44 of the other fermenters.

Specific details of an exemplary control strategy implemented by the cooling system control system 40 of FIG. 4 are described below, but a general overview of the events of a typical fermenter batch is provided first. When the fermenter 20 is first charged, there may be little to no fermentation reaction as the contents are circulated. Thus, no cooling is needed and the control system 40 may keep both cooling tower 110 and chiller water 120 control valves closed. As the fermentation reaction proceeds, the bulk temperature indicated by sensor 102 may gradually increase. However, the rate of increase of the recirculation temperature indicated by sensor 106 may be greater than that of the bulk temperature. In addition, the recirculation temperature may be less sensitive to outside disturbances, such as air temperature fluctuations and changes in air humidity, than the bulk temperature. Thus, embodiments of the control system 40 may use the recirculation temperature sensor 106 to control fermenter cooling instead of the bulk temperature sensor 102. Once the recirculation temperature reaches a predetermined setpoint, the control system 40 may begin to open cooling tower control valve 110 to keep the recirculation temperature at or near the predetermined setpoint. As the heat from the fermentation reaction increases, the control system 40 may open the cooling tower control valve 110 more to maintain the recirculation temperature at or near the setpoint. Cooling tower water 24 alone may be sufficient to keep the recirculation temperature at or near the setpoint, but certain events may increase cooling demand. For example, during warm periods of the year, the temperature of the cooling tower water 24 may be higher than normal because of higher ambient air temperatures. Such warm cooling tower water 24 may not remove the heat of fermentation as easily as cooler water. Additionally, the capacity of the cooling tower 26 may be limited. If several other fermenters 20 are operating at points during a batch where cooling demand is increased, then there may be an insufficient supply of cooling tower water 24 for all of the fermenters 20.

When the control system 40 determines that cooling tower water system has reached its limit (e.g. when cooling tower water control valve 110 is completely open), the control system 40 may either turn on the chiller 30 or send a signal to operators to turn it on manually. At this point, the control system 40 may direct chiller water control valve 120 to gradually open to help keep the recirculation temperature at or near the setpoint. Because of the lower temperature of the chiller water 28, the cooler 22 may operate more effectively to remove the heat of fermentation. As the control system 40 opens chiller water control valve 120, it may gradually close cooling tower water control valve 110, depending on the piping configuration and water temperatures. For example, depending on the piping configuration and water temperatures, if the cooling tower water control valve 110 is kept completely open, the chiller water 28 may not have as great an effect to reduce the recirculation temperature. This phenomenon is discussed in more detail below with respect to FIG. 6. If the recirculation temperature continues to increase, the control system 40 may open the chiller water control valve 120 completely. At this point, the control system 40 may determine the states of the other fermenters 20 in their batches and prioritize the fermenters 20 based on how far their recirculation temperatures are from setpoint (if at all). The control system 40 may then direct some or all of the chiller water 28 to the fermenter or fermenters 20 with the highest priority, i.e. those farthest from the recirculation temperature setpoint. In this way, the control system 40 attempts to minimize the potential negative effects to the entire biofuel production plant 10 of a fermenter 20 with an uncontrolled recirculation temperature, namely the possible loss of yeast and resulting economic loss. In general, then, the system operates to balance the supply of both cooling tower water and chiller water to multiple fermenters based upon their relative needs (e.g., temperatures) to optimize productivity, yield and efficiency. Also, the control scheme may allow for special prioritization of cooling of one or more fermenters that reach or approach a particularly elevated temperature at which the yeast may be in danger of death that could lead to actual loss of some or all of a batch in the particular fermenter.

Figure 5:
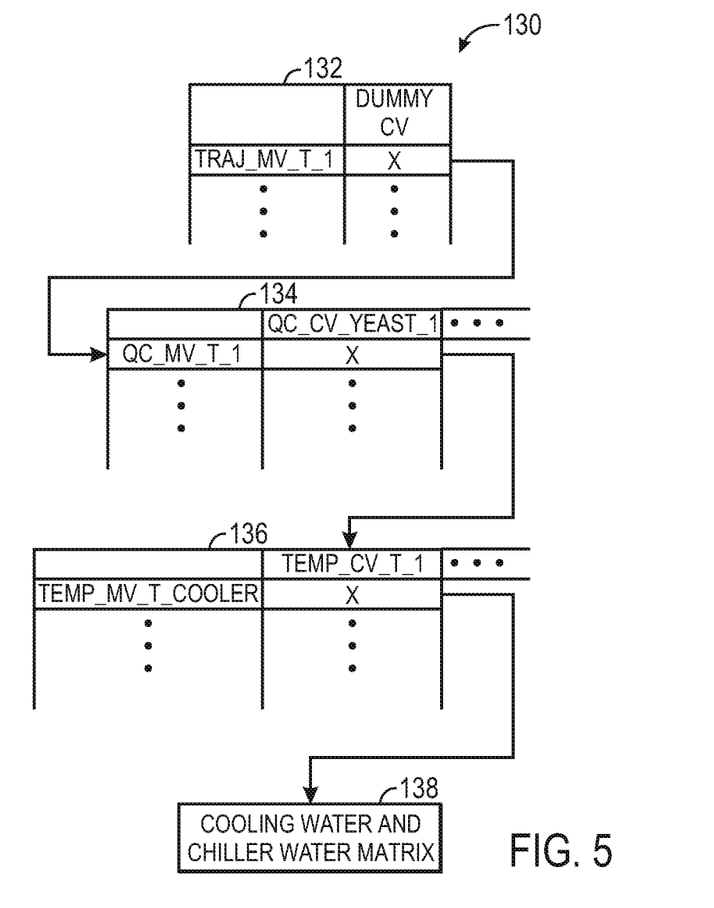
FIG. 5 is a diagram of a cascaded nonlinear model predictive control (MPC) structure for determining fermenter temperature according to an embodiment.

FIG. 5 shows part of an exemplary cascaded nonlinear MPC structure 130, along with an overlaying quality controller that determines the fermenter temperature. In other embodiments, the MPC structure 130 may represent linear process relationships. The MPC structure 130 is an example of the processing circuitry 54 that may be used to control the operation of the biofuel production plant 10. Each of the tables shown in FIG. 5 represents an individual matrix of the MPC structure 130. Each matrix represents relationships between various measured or calculated process parameters. In a typical matrix, the first column on the left lists various MV's utilized by that matrix. In addition, any disturbance variables (DV's), which represent variables that affect CV's but which the MPC structure 130 cannot manipulate, are also listed in the first column. Next, the top row of the matrix lists CV's that have a relationship with one or more of the MV's and/or DV's. An "X" at the intersection of a particular MV/DV and CV pair indicates that a relationship exists between the two. In other words, changes in the MV or DV will result in a change in the CV. If there is no X at the intersection, then changes in the MV or DV will not result in any change in the CV. In other words, there is no relationship between that MV/DV and CV pair. Vertical and horizontal ellipses indicate that there are other MV's/DV's or CV's in the matrix, but that they are not shown for clarity or convenience.

In the trajectory matrix 132 of FIG. 5, TRAJ_MV_T_1 represents a trajectory of the fermenter bulk temperature 102. In other words, TRAJ_MV_T_1 represents what the model 82 predicts will be the desired future setpoints for the fermenter bulk temperature 102 over a particular period. The trajectory is a MV as the model 82 can change it to bring about a desired change in a CV. Here, TRAJ_MV_T_1 only has a relationship with a dummy CV. In other words, the dummy CV is not an actual variable that is being controlled, but instead is a placeholder variable to be used as an input to another matrix. Here, that other matrix is quality matrix 134. The line from trajectory matrix 132 to quality matrix 134 represents a MV trajectory going to the desired value of the MV. Here, the MV desired value is QC_MV_T_1, which represents the fermenter bulk temperature 102 being used to control the CV's of the quality matrix 134. As shown, there is a relationship between QC_MV_T_1 and QC_CV_YEAST_1, which represents the health of the yeast in the fermenter 20. Yeast performs best in a certain temperature range. If the temperature is too low, the yeast will perform sluggishly, resulting in a low fermenter yield. If the temperature is too high, the yeast may be damaged, resulting in a low or nonexistent fermenter yield. Thus, the fermenter bulk temperature 102 is manipulated to keep the yeast in a healthy range.

Next, the line from quality matrix 134 to fermenter temperature matrix 136 in FIG. 5 represents a MV trajectory going to the CV desired value. Here, TEMP_MV_T_COOLER represents the recirculation temperature 106. As shown, there is a relationship between TEMP_MV_T_COOLER and TEMP_CV_T_1, which represents the controlled fermenter bulk temperature. Thus, the recirculation temperature is manipulated to have the fermenter bulk temperature follow the trajectory of the bulk temperature coming from the quality matrix 134. This is an example of cascade control, in which an outer loop controller controls a primary parameter and an inner loop controller receives a setpoint from the outer loop controller to control a secondary parameter. Here, the temperature control of the fermenter bulk temperature is the outer loop and sends a setpoint to the temperature control of the recirculation temperature, which is the inner loop. Finally, the line from fermenter temperature matrix 136 to cooling water and chiller water matrix 138 represents the MV trajectory of the recirculation temperature going to the CV desired value.

Figure 6:
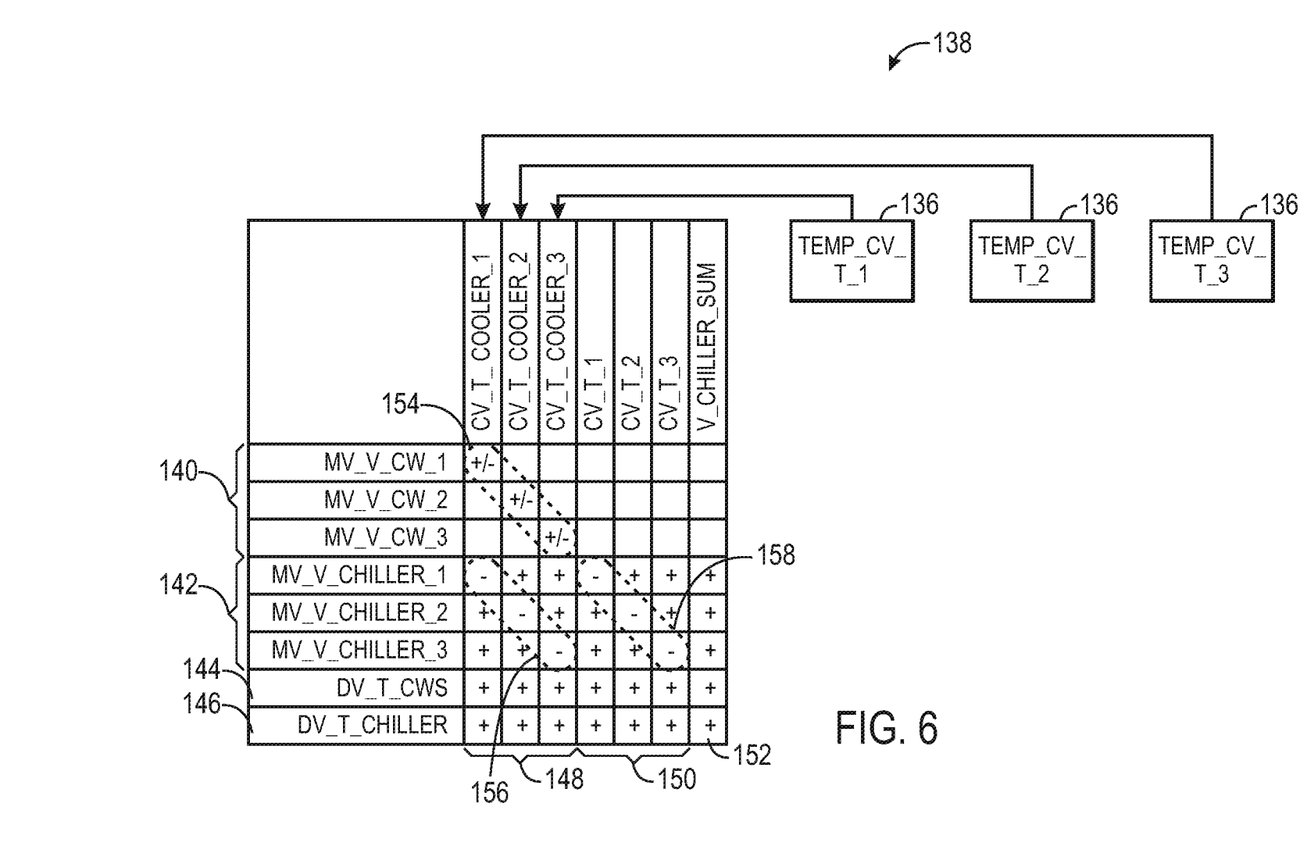
FIG. 6 is a diagram of a cooling water and chiller water matrix of the MPC structure of FIG. 5 according to an embodiment.

FIG. 6 shows the cooling water and chiller water matrix 138 for an exemplary system that includes three fermenters 20. In this matrix, the X's indicating relationships have been replaced with positive or negative signs. A positive sign represents a positive relationship. In other words, an increase in the MV will result in an increase in the CV. Correspondingly, a negative sign indicates a negative relationship, where an increase in MV results in a decrease in the CV or vice versa. The three trajectories of the recirculation temperatures for the fermenters 20 are shown coming from fermenter temperature matrices 136. These pass to the first group of CV's 148, starting with CV_T_COOLER_1, which represents the controlled recirculation temperatures. The second group of CV's 150, starting with CV_T_1, represents high bulk temperature limits above which yeast death may occur. Accordingly, the high temperature limits are higher than the normal setpoints for the bulk temperatures. Finally, the last CV 152, V_CHILLER_SUM, represents the summation of the valve positions of all the chiller control valves 120. For example, if the first chiller control valve 120 is 10% open, the second is 20% open, and the third is 40% open, then V_CHILLER_SUM equals 70%. Thus, V_CHILLER_SUM provides an indication of the how much of the capacity of the chiller 30 is being used and may range from a minimum of approximately 0% to a maximum of approximately 300% for a biofuel production plant 10 with three fermenters 20. As described above, the chiller 30 may have a minimum operating flow rate, which may correspond to a specified value for V_CHILLER_SUM. Below this minimum value of V_CHILLER_SUM, the control system 40 may turn off or shut down the chiller 30 or send an instruction to the operators to do the same.

The first group of MV's 140, starting with MV_V_CW_1, represents the manipulated cooling tower water control valve 110 position. As shown, positive and negative relationships 154 exist between the cooling tower water control valve 110 position and the corresponding recirculation temperature for each fermenter 20, such as between MV_V_CW_1 and CV_T_COOLER_1. The reasoning for positive and negative relationships 154 is discussed below. However, there is no relationship between the cooling tower water control valve 110 position for a particular fermenter and the recirculation temperature 106 of other fermenters, such as between MV_V_CW_1 and CV_T_COOLER_2, as each fermenter 20 is only cooled by its own cooler 22. In addition, there is no relationship shown between the group 140 of cooling tower water control valve 110 positions and the group 150 of high bulk temperature limits because such high temperatures occur when cooling tower water 24 alone is insufficient for cooling and chiller water 28 is needed. Finally, there is no relationship between the group 140 and the summation of chiller valve positions, V_CHILLER_SUM.

Returning to the first group of CV's 148, when only cooling tower water 24 is used for cooling, an increase in the valve position of the cooling tower water control valve 110 will cause more water to flow through the cooler 22 and decrease the recirculation temperature. This is a negative relationship, or a negative acting state. However, when both cooling tower water 24 and chiller water 28 are being used, an increase in valve position of the cooling tower water control valve 110 may increase the recirculation temperature—a positive relationship, or positive acting state, depending on the piping configuration and water temperatures. This unexpected result may occur when cooling tower water 24 and chiller water 28 are used together in response to insufficient cooling of the fermenter 20 with cooling tower water 24 alone. Because the capacity of water piping is limited and the flow rate of cooling tower water 24 may be greater than that of chiller water 28, increasing the flow rate of cooling tower water 24 may cause the flow rate of chiller water 28 to decrease, depending on the piping configuration and water temperatures. In other words, the chiller water 28 may be "backed off" by the greater flow rate of cooling tower water 24. Because the cooler chiller water 28 is what may decrease the fermenter temperature, the decrease in the flow rate of chiller water 28 causes the fermenter temperature to increase. In certain embodiments, the model 82 may be programmed to recognize both positive and negative relationships between groups 140 and 148 and to respond accordingly. For example, the model 82 may indicate that a completely open cooling tower control valve 110 should be gradually closed as the chiller water control valve 120 opens.

The second group of MV's 142 in FIG. 6, starting with MV_V_CHILLER_1, represents the MV of chiller water control valve 120 position. Unlike the first group 140 of MV's, relationships exist between all of the MV's in the second group 142 and all of the CV groups 148, 150, and 152. Turning first to group 148, negative relationships 156 exist between the chiller water control valve position 120 and the corresponding controlled recirculation temperature for each fermenter 20. In other words, as more chilled water 28 passes through the cooler 22 resulting from increasing the control valve 120 position, more heat is removed and the recirculation temperature decreases. Positive relationships exist outside of the valve position 120 and recirculation temperature pair for each fermenter 20. In other words, if more chilled water 28 is directed to the first cooler, for example, then because the capacity of the chiller 30 may be fixed, less chilled water 28 is available for the second and third coolers and the recirculation temperatures for those fermenters 20 will increase. Similar relationships exist between the second group 142 of MV's and the second group 150 of CV's. Here, increasing the chiller water control valve 120 position will move the bulk temperature away from the high temperature limit. In addition, directing more chiller water 28 to the first cooler, for example, moves the bulk temperatures of the other two fermenters toward the high temperature limit. Finally, there is a positive relationship between the second group 142 of MV's and V_CHILLER_SUM. As any of the chiller water control valve 120 positions increase, the sum of all the chiller valve positions 152 will also increase.

The last two entries in the cooling water and chiller water matrix 138 of FIG. 6 represent the relationship between DV's and the CV's. Specifically, the first DV 144, DV_T_CWS, represents the cooling tower water supply temperature indicated by sensor 108. This is a DV and not an MV because operation of the cooling tower 26 is affected by ambient air temperature, which cannot be effectively manipulated. A positive relationship exists between DV 144 and all of the CV's 148, 150, and 152. As the cooling tower water supply temperature increases, the temperature gradient available in the coolers 22 decreases, resulting in the removal of less heat of fermentation. Thus, the recirculation temperatures may increase and the bulk temperatures may move closer to the high temperature limits. In addition, the sum of all the chiller valve positions 152 will increase because more chiller water 28 may be needed to counteract the effect of warmer cooling tower water 24. The second DV 146, DV_T_CHILLER, represents the chiller water supply temperature indicated by sensor 116. This is a DV and not an MV because the chiller 30 is supplied with cooling tower water 24 and may have a fixed cooling capacity. As the cooling tower water supply temperature increases, the chiller water supply temperature may increase as well. Because of this, positive relationships exist between DV 146 and CV's 148, 150, and 152 for the same reasons as for DV 144.

Figure 7:
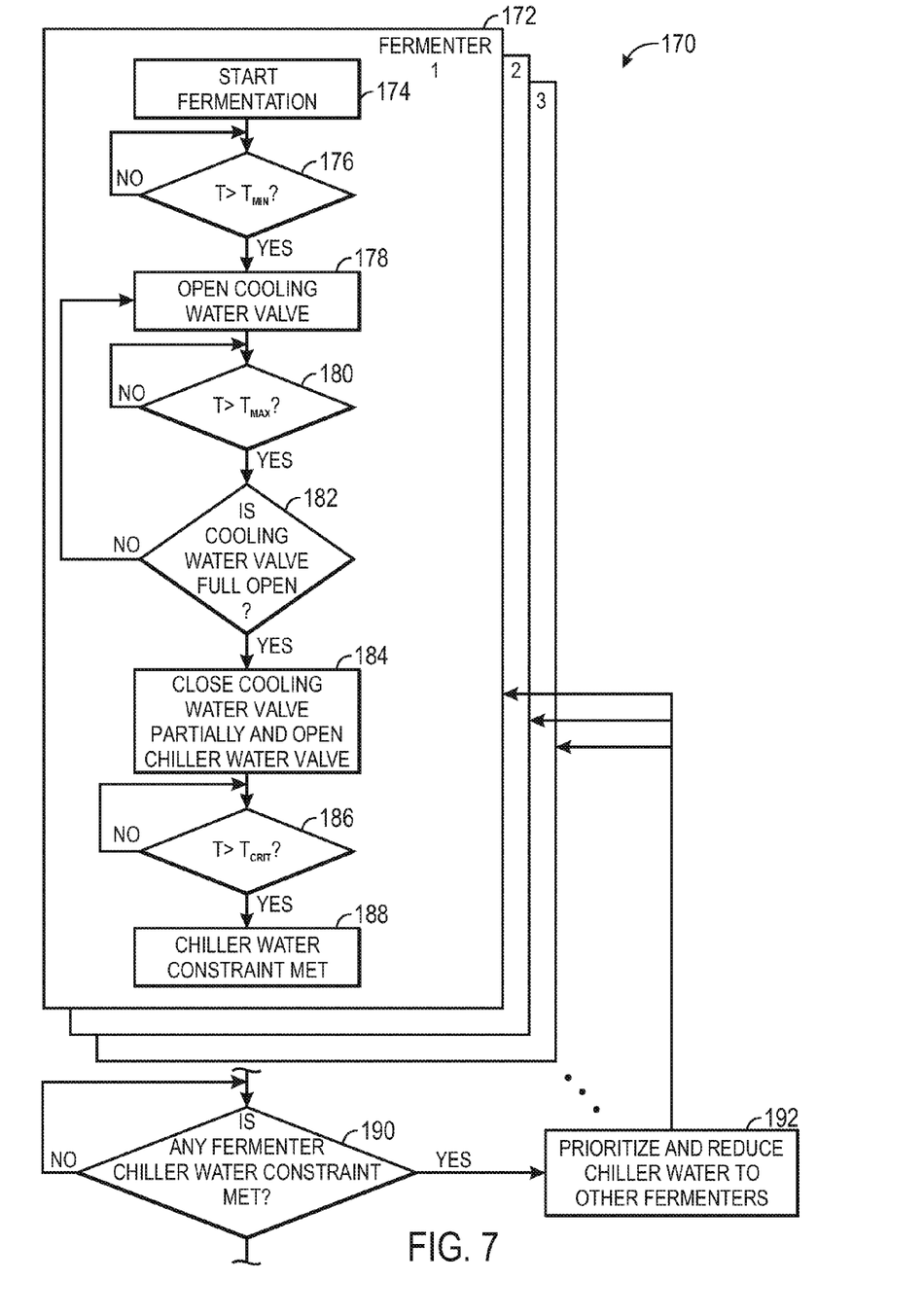
FIG. 7 is a flowchart of an exemplary method for controlling a fermenter cooling system.

FIG. 7 is a flowchart of an exemplary method 170 for a cooling system control scheme that may be implemented by the cooling system control system 40. An embodiment of the invention may be embodied in the form of computer-implemented processes and apparatuses for practicing those processes. Embodiments of the present invention may also be embodied in the form of a computer program product having computer program code containing instructions embodied in tangible media, such as floppy diskettes, CD-ROMs, hard drives, USB (universal serial bus) drives, or any other computer readable storage medium, wherein, when the computer program code is loaded into and executed by a computer, the computer becomes an apparatus for practicing embodiments of the invention. Embodiments of the invention also may be embodied in the form of computer program code, for example, whether stored in a storage medium, loaded into and/or executed by a computer, or transmitted over some transmission medium, such as over electrical wiring or cabling, through fiber optics, or via wireless transmission, wherein when the computer program code is loaded into and executed by a computer, the computer becomes an apparatus for practicing embodiments of the invention. When implemented on a general-purpose processor, the computer program code segments configure the processor to create specific logic circuits. A technical effect of the method 170 may include, among others, the controlling of the cooling of parallel-operated batch processes in a biofuel production plant 10 using a cooling system that includes one or more cooling fluids.

Specifically, the cooling system control system 40 may include computer code disposed on a computer-readable storage medium or a process controller that includes such a computer-readable storage medium. The computer code may include instructions for optimizing the cooling of one or more fermenters 20 in a biofuel production plant 10 using a cooling system that includes cooling tower water 24 and chiller water 28. In other embodiments, the computer code may include additional instructions. For example, the code may include instructions for determining an economic cost of energy utilized within the cooling system and determining an economic value of products produced by the biofuel production plant 10. In other embodiments, the instructions for determining optimal target values for the flow rates of the cooling fluids may be based on the economic cost and economic value determinations. In further embodiments, the code may include instructions for measuring the operating variables using process instruments or for cyclically repeating certain instructions.

Returning to FIG. 7, each fermenter 20 may have its own cooling system control scheme 172 that is identical to the schemes for all the fermenters 20. However, each of the schemes 172 may be operating at different steps depending on what stage the fermenter 20 for that scheme 172 is at in its batch. First, step 174 represents the beginning of the fermentation batch. Step 174 may include charging the fermenter 20 with mash, yeast, and/or other additives and circulating the contents with the circulating pump. Next, in decision block 176, the temperature T of the fermenter 20 is compared with a minimum temperature $T_{MIN}$. For the MPC structure 130 described above, the temperature T may be the recirculation temperature indicated by sensor 106. If T is less than $T_{MIN}$, then fermentation continues. If T is greater than $T_{MIN}$, then cooling tower water valve 110 opens in step 178. Next, in decision block 180, T is compared with a maximum temperature $T_{MAX}$. If T is less than $T_{MAX}$, then fermentation continues. If T is greater than $T_{MAX}$, then decision block 182 determines whether the cooling tower water valve 110 is completely open. If not, the cooling tower water valve 110 is opened more in step 178. If the valve 110 is completely open, then in step 184, valve 110 may be closed partially and the chiller water control valve 120 opened, depending on the piping configuration and water temperatures. As described above, if the cooling tower water valve 110 is not partially closed, then the chiller water 28 may not be able reduce T, depending on the piping configuration and water temperatures. In decision block 186, if T is greater than a critical, or threshold, temperature $T_{CRIT}$, which may correspond to the high bulk temperature limits 150 at which yeast death may begin, then a chiller water constraint in block 188 will be met. Otherwise, fermentation will continue.

Operating outside of the individual cooling system control schemes 172 may be additional steps and decision blocks. For example, in decision block 190, if the chiller water constraint is met for any fermenter 20, then the fermenters 20 are prioritized in step 192 and the flow rate of chiller water 28 is reduced to lower priority fermenters. As yeast death may be a negative impact for a biofuel production plant 10, such prioritization may reduce the possibility of such an event at the cost of operating other fermenters 20 at higher than desired temperatures that are still less than $T_{CRIT}$. Running at a temperature higher than desired but less than $T_{CRIT}$ may reduce fermenter yield, but may be a better alternative than allowing any yeast in the biofuel production plant 10 to perish.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A biofuel production system, comprising:
   a plurality of parallel-operated fermenters;
   a cooling tower water system configured to supply cooling water to the plurality of parallel-operated fermenters and comprising a plurality of cooling tower water control valves configured to meter the cooling water to each of the plurality of parallel-operated fermenters;
   a chiller water system configured to supply chiller water to the plurality of parallel-operated fermenters and comprising a plurality of chiller water control valves configured to meter the chiller water to each of the plurality of parallel-operated fermenters; and
   a cooling system coupled to the plurality of parallel-operated fermenters, the cooling tower water system, and the chiller water system, wherein the cooling system controls the flow rates of the cooling water and the chiller water to the plurality of parallel-operated fermenters by adjusting the plurality of cooling tower water control valves and the plurality of chiller water control valves to control a recirculation temperature.

2. The biofuel production system of claim 1, comprising a computer-readable storage medium, comprising computer code disposed on the computer-readable storage medium, wherein the code comprises instructions for determining desired flow rates of the cooling water and the chiller water, the instructions comprising:
   instructions for determining operating variables of the plurality of parallel-operated fermenters and the cooling system;
   instructions for determining constraints of the plurality of parallel-operated fermenters and the cooling system;
   instructions for determining desired flow rates of the cooling water and the chiller water through the plurality of parallel-operated fermenters based upon the determined operating variables, constraints, and overall optimization objective; and
   instructions for controlling the flow rates of the cooling water and the chiller water through the plurality of parallel-operated fermenters based upon the desired flow rate determinations.

3. A biofuel production system, for use in a facility having a plurality of parallel-operated fermenters, a cooling tower water system, and a chiller water system, the biofuel production system comprising:
   a cooling system coupled to the plurality of parallel-operated fermenters, the cooling tower water system, and the chiller water system, wherein the cooling system controls the flow rates of the cooling water and the chiller water to the plurality of parallel-operated fermenters by adjusting a plurality of cooling tower water control valves configured to meter the cooling water to each of the plurality of parallel-operated fermenters and a plurality of chiller water control valves configured to meter the chiller water to each of the plurality of parallel-operated fermenters; and
   a process controller configured to determine desired flow rates of the cooling water and the chiller water to each of the parallel-operated fermenters, wherein the flow rate of the cooling water has a negative relationship with the flow rate of the chiller water.

4. The biofuel production system of claim 3, wherein the process controller comprises:
   instructions for determining operating variables of the plurality of parallel-operated fermenters and the cooling system;
   instructions for determining constraints of the plurality of parallel-operated fermenters and the cooling system;
   instructions for determining desired flow rates of the cooling water and the chiller water through the plurality of parallel-operated fermenters based upon the determined operating variables, constraints, and overall optimization objective; and
   instructions for controlling the flow rates of the cooling water and the chiller water through the plurality of parallel-operated fermenters based upon the desired flow rate determinations.

5. The biofuel production system of claim 4, wherein the process controller comprises instructions for determining an economic cost of energy utilized within the cooling system and determining an economic value of products produced by the biofuel production system.

6. A biofuel production system, comprising:
   a plurality of parallel-operated fermenters;
   a cooling tower water system configured to supply cooling water to the plurality of parallel-operated fermenters and comprising a plurality of cooling tower water control valves configured to meter the cooling water to each of the plurality of parallel-operated fermenters;
   a chiller water system configured to supply chiller water to the plurality of parallel-operated fermenters and comprising a plurality of chiller water control valves configured to meter the chiller water to each of the plurality of parallel-operated fermenters; and
   a cooling system coupled to the plurality of parallel-operated fermenters, the cooling tower water system, and the chiller water system, wherein the cooling system controls supply of the cooling water and/or the chiller water to the parallel-operated fermenters during normal operation by adjusting the plurality of cooling tower water control valves and/or the plurality of chiller water control valves to control a recirculation temperature, and provides prioritized supply of the chiller water from the chiller water system to any fermenter with a temperature approaching or meeting a threshold temperature by adjusting the plurality of chiller water control valves.

7. The biofuel production system of claim 6, comprising a computer-readable storage medium, comprising computer code disposed on the computer-readable storage medium, wherein the code comprises instructions for determining desired flow rates of the cooling water and the chiller water, the instructions comprising:
   instructions for determining operating variables of the plurality of parallel-operated fermenters and the cooling system;

instructions for determining constraints of the plurality of parallel-operated fermenters and the cooling system;

instructions for determining desired flow rates of the cooling water and the chiller water through the plurality of parallel-operated fermenters based upon the determined operating variables, constraints, and overall optimization objective; and instructions for controlling the flow rates of the cooling water and the chiller water through the plurality of parallel-operated fermenters based upon the desired flow rate determinations.

8. The biofuel production system of claim 6, wherein the threshold temperature corresponds to a temperature at which accelerated death of yeast occurs.

9. The biofuel production system of claim 6, wherein the cooling system provides prioritized supply of water from the chiller water system to any fermenter with a temperature approaching or meeting a threshold temperature when a determined desired flow rate of cooling water exceeds a capacity of the cooling tower water system.

10. A biofuel production system, for use in a facility having a plurality of parallel-operated fermenters, a cooling tower water system, and a chiller water system, the biofuel production system comprising:

a cooling system coupled to the plurality of parallel-operated fermenters, the cooling tower water system, and the chiller water system, wherein the cooling system controls the flow rates of the cooling water and the chiller water to the plurality of parallel-operated fermenters by adjusting a plurality of cooling tower water control valves configured to meter the cooling water to each of the plurality of parallel-operated fermenters and a plurality of chiller water control valves configured to meter the chiller water to each of the plurality of parallel-operated fermenters; and a process controller configured to determine desired flow rates of the cooling water and the chiller water to each of the parallel-operated fermenters, wherein the flow rate of the cooling water has a negative relationship with the flow rate of the chiller water, and to provide prioritized supply of the chiller water from the chiller water system to any fermenter with a temperature approaching or meeting a threshold temperature.

11. The biofuel production system of claim 10, wherein the process controller comprises:

instructions for determining operating variables of the plurality of parallel-operated fermenters and the cooling system;

instructions for determining constraints of the plurality of parallel-operated fermenters and the cooling system;

instructions for determining desired flow rates of the cooling water and chiller water through the plurality of parallel-operated fermenters based upon the determined operating variables, constraints, and overall optimization objective; and instructions for controlling the flow rates of the cooling water and chiller water through the plurality of parallel-operated fermenters based upon the desired flow rate determinations.

12. The biofuel production system of claim 10, wherein the threshold temperature corresponds to a temperature at which accelerated death of yeast occurs.

13. The biofuel production system of claim 10, wherein the process controller comprises instructions for determining the desired flow rates of the cooling water and chiller water based at least in part upon controlling a fermenter recirculation temperature and/or a fermenter tank temperature.

14. The biofuel production system of claim 10, wherein the process controller comprises instructions for controlling the flow rates of the cooling water and chiller water automatically.

15. The biofuel production system of claim 10, wherein the process controller comprises instructions for maintaining automatic control of the cooling tower water control valves that change between positive acting and negative acting states.

16. The biofuel production system of claim 10, wherein the process controller comprises instructions for turning off the chiller water system when the determined desired flow rate of chiller water is less than a specified minimum operating flow rate of the chiller water system.

17. The biofuel production system of claim 10, wherein the process controller comprises instructions for directing chiller water to the one or more fermenters furthest from a temperature setpoint when the determined desired flow rate of chiller water exceeds a capacity of the chiller water system.

18. The biofuel production system of claim 17, wherein the process controller comprises instructions for determining the temperature setpoint based on a stage of a fermenter batch.

19. A method for controlling the cooling of a plurality of parallel-operated batch processes in a production plant using a cooling system comprising a plurality of cooling fluids, comprising:

(a) determining operating variables of the plurality of parallel-operated batch processes and the cooling system;

(b) determining constraints of the plurality of parallel-operated batch processes and the cooling system;

(c) determining desired flow rates of the plurality of cooling fluids through the plurality of parallel-operated batch processes based upon the determined operating variables, constraints, and an overall optimization objective, wherein a first flow rate has a negative relationship with a second flow rate; and (d) controlling the flow rates of the plurality of cooling fluids through the plurality of parallel-operated batch processes based upon the desired flow rate determinations by adjusting a plurality of cooling fluid control valves configured to meter each of the plurality of cooling fluids to each of the plurality of parallel-operated batch processes.

20. The method of claim 19, wherein the constraints of the plurality of parallel-operated batch processes and the cooling system include process constraints, energy constraints, equipment constraints, legal constraints, operator-imposed constraints, or a combination thereof.

21. The method of claim 19, comprising determining operating variables of other processes in the production plant, for use in step (c).

22. The method of claim 19, comprising utilizing inferential models for determining the operating variables of the plurality of parallel-operated batch processes and the cooling system.

23. The method of claim 19, wherein step (c) comprises predictive control and optimization of the flow rates of the plurality of cooling fluids utilizing model-based techniques, wherein the predictive control and optimization comprises:

deriving measurements from process instruments, utilizing inferential models, using laboratory values, or a combination thereof; and executing linear or nonlinear prediction models to obtain an overall optimization objective subject to dynamic constraints of the plurality of parallel-operated batch processes and the cooling system.

24. The method of claim 23, wherein the overall optimization objective is to reduce energy costs per unit mass of product produced by the production plant.

25. The method of claim 23, wherein the overall optimization objective is to achieve a target or maximum throughput through the production plant.

* * * * *